United States Patent
Sleeman et al.

(10) Patent No.: US 6,391,301 B1
(45) Date of Patent: May 21, 2002

(54) AGENT FOR IDENTIFYING AND TREATING METASTASIZING TUMORS

(75) Inventors: Jonathan Sleeman, Bruchsal; Helmut Ponta, Weingarten; Peter Herrlich, Karlsruhe, all of (DE); Kim Untae, Snyder, NY (US)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 0 days.

(21) Appl. No.: 09/319,810

(22) PCT Filed: Dec. 18, 1997

(86) PCT No.: PCT/EP97/07105

§ 371 Date: Aug. 16, 1999

§ 102(e) Date: Aug. 16, 1999

(87) PCT Pub. No.: WO98/26801

PCT Pub. Date: Jun. 25, 1998

(30) Foreign Application Priority Data

Feb. 12, 1998 (DE) .......................... 196 52 815

(51) Int. Cl.⁷ ...................... A61K 39/395; C07K 16/28; C07K 16/30; C07K 16/34
(52) U.S. Cl. ................. 424/155.1; 424/138.1; 424/141.1; 424/137.1; 424/152.1; 424/153.1; 424/172.1; 424/174.1; 424/175.1; 530/388.8; 530/388.7; 530/388.1; 530/387.5; 530/387.7
(58) Field of Search ............... 530/387.1, 388.1, 530/388.7, 389.1, 389.6, 389.7, 388.8, 387.7, 387.5; 424/130.1, 137.1, 153.1, 155.1, 173.1, 174.1, 138.1, 141.1, 152.1, 172.1, 175.1

(56) References Cited

PUBLICATIONS

Furukawa, K. et al. Analysis of the fine specificities of 11 mouse monoclonal antibodies reactive with type 2 blood group determinants. Molecular Immunology 27(8): 723–732, 1990.*

Laferte, S. et al. Monoclonal antibody recognizing a determinant of type 2 chain blood group A and b oligosaccharides detects oncodevelopmental changes in azoxymethane–induced rat colon tumors and human colon cancer cell lines. Journal of Cellular Bioch, 1995.*

Ernst, C.S. et al. Multiparameter evaluation of the expression in situ of normal and tumor–associated antigens in human colorectal carcinoma. J. Nat. Cancer Inst. 77(2): 387–395, Aug. 1986.*

Fiszman, G. et al. Immunological characterization of blood group A epitopes expressed on cells and tissues with a monoclonal anti–cea antibody. Haematologica, 79: 112–118, 1994.*

K. Myers et al: "Isolation of A cDNA Encoding 5T4 Oncofetal Trophobast Glycoprotein" The Journal of Biological Chemistry, BD. 269, No. 12, Mar. 25, 1994.

J. Sleeman: "Blutgruppenantigene ALS Metastasierungsmarker Und Auslöser Des Aktiven Zellotods" Nachrichten Forschungszentrum Karlsruhe, Bd. 29, No. 2.

* cited by examiner

*Primary Examiner*—Anthony C. Caputa
*Assistant Examiner*—Anne L. Holleran
(74) *Attorney, Agent, or Firm*—Friedrich Kueffner (57) ABSTRACT

The present invention relates to a novel composition for identifying and suppressing the growth of tumor cells, which comprises antibodies which react with proteins having N-glycosidically bonded saccharides.

5 Claims, 8 Drawing Sheets

Metastasizing — Non-metastasizing

Fig. 4

M-N#1 expression during mammary gland regression following lactation

Fig. 5

M-N#1 expression during prostate regression

Fig.7
The M-N#1 antigen is fucosylated

Fig. 8

AGENT FOR IDENTIFYING AND TREATING METASTASIZING TUMORS

BACKGROUND OF THE INVENTION

1. Field of the Invention

The present invention relates to a composition for identifying and suppressing the growth of tumor cells.

2. Description of the Related Art

One of the commonest causes of illness in the western world is the occurrence of malignant tumors. Early diagnosis of tumors and subsequent treatment thereof is still problematical. A number of markers for identifying tumor growth and the formation of metastases have been described in recent years (cf. Potter-Jordan, K. and Lippman,. M., Hematol. Oncol. Clin. North Am. 8, 73 to 100 (1994)). Some of these markers, for example erbE-2, cathepsin D, have proved to be very useful in a large number of studies. Very recently, variants of the protein CD44 have become important (Kaufmann et al. Lancet 345, 615 to 619 (1995), EP 0531300, DE-A 4134982). Finally, EP 351313, CA121: 29448, CA 115: 69417, Medline 95085293, CA 111: 209896 disclose antigen-antibody systems using proteins comprising N-glycosidically bonded saccharides. It is known on the basis of these publications that poly- or monoclonal antibodies which specifically recognize particular epitopes on the tumor marker proteins and react therewith, and which can be labeled by radioisotopes and/or be conjugated with substances with cytocidal or cytotoxic activity can be used for diagnosing and treating metastasizing tumors.

Antibodies respond to specific epitopes. As a rule, different tumors express different markers and, on the other hand, one marker always covers only one subset. It is therefore desirable to have a plurality of different markers for tumor control within the framework of multicomponent treatment.

SUMMARY OF THE INVENTION

It was accordingly an object of the present invention to develop a composition for identifying and for suppressing the growth of tumors which can, if possible, be employed equally well for different tumors.

This object is achieved by a composition for identifying and suppressing the growth of tumor cells comprising antibodies which react with proteins comprising N-glycosidically bonded saccharides, wherein the saccharides belong to the blood group-specific antigens of type B2, 3, 4 or type A2.

Suitable for the purposes of the invention is any appropriate variant of proteins of animal or human origin modified with the specific saccharides.

The term antibody means mono- or polyvalent antibodies and poly- and monoclonal antibodies, but also those representing fragments thereof and derivatives thereof, including the $F(ab')_2$, Fab' and Fab fragments, but also chimeric antibodies or hybrid antibodies having at least two antigen or epitope binding sites, or bispecific recombinant antibodies (for example quadromas, triomas), interspecies hybrid antibodies, anti-idiotype antibodies and, of these, those which have been chemically modified and are to be regarded as derivatives of these antibodies and which can be produced either by the known conventional methods for obtaining antibodies or by DNA recombination, via hybridoma techniques or antibody engineering or synthetically or semisynthetically in a manner known per se and have neutralizing or binding properties in relation to the sugar chains described and defined above. From the diverse literature, reference may be made only by way of example to studies by Köhler, G. & Milstein, C., Nature 256, 495 to 497, 1975; Biocca, S. et al., Embo, J. 9, 101 to 108, 1990; Bird, R. E. et al., Science 242, 423 to 426, 1988; Boss, M. A. et al., Nucl. Acids Res. 12, 3791 to 3806, 1984; Boulianne, G. L. et al., Nature 312, 643 to 646, 1984; Bukovsky, J. & Kennett, R. H., Hybridoma 6, 219 to 228, 1987; Diano, M. et al., Anal. Biochem. 166, 223 to 229, 1987; Huston, J. S. et al., Proc. Natl. Acad. Sci. USA 85, 5879 to 5883, 1988; Jones, P. T. et al., Nature 321,, 522 to 525, 1986; Langone, J. J. & Vunakis, H. V. (ed.), Methods Enzymol, 121, Academic Press, London, 1987; Morrison S. et al., Proc. Natl. Acad. Sci. USA 81, 6851 to 6855, 1984; Oi, V. T. & Morrison, S. L., Bio Techniques 4, 214 to 221, 1986; Riechmann, L. et al., Nature 332, 323 to 327, 1988; Tramontano, A. et al., Proc. Natl. Acad. Sci. USA 83, 6736 to 6740, 1986; Wood, C. R. et al., Nature 314, 446 to 449, 1985.

Concerning the production of polyclonal antibodies against epitopes, a number of methods are available. It is possible for this purpose, for example, to immunize in a manner known per se various animals by injection with the glycoprotein according to the invention, or fragments thereof, and to isolate and purify the required polyclonal antibodies by known methods from the sera obtained thereby. It is likewise possible to use various adjuvants to increase the immune response to the protein administration, depending on the animal selected for the immunization—for example Freund's adjuvant, mineral gels such as, for example, aluminum hydroxide, surface-active substances such as, for example, polyanions, peptides, oil emulsions, hemocyanins, dinitrophenol or lysolecithin. Monoclonal antibodies are preferred according to the invention. The antibody M-N#1 is particularly preferred and can be obtained from the cell culture DSM ACC 2333 which is deposited at the DSMZ, Deutsche Sammlung von Mikroorganismen und Zellkulturen GmbH, Braunschweig.

The monoclonal antibodies preferred for the use according to the invention can be obtained by any appropriate technique available for producing antibodies by cultivation of cell lines. The known techniques of this type include, for example, the methods described by Köhler, G. and Milstein, C., 1975, loc. cit., or Taggart & Samloff, Science 219, 1228 to 1230, 1983, with hybridoma cells or those with human B cell hybridomas (Kozbor et al., Immunology Today 4, 72 to 79, 1983). These methods also include the use of gene libraries from B lymphocytes (Ward et al., 1989; Nature 341, 544–546) and "combinatorial" libraries on phage vectors (McCafferty et al., 1990, Nature 348, 552–554; Krang et al., 1991, PNAS88, 4363–4366).

The antibodies can be purified by known methods, for example by immunoabsorption or immunoaffinity chromatography, by HPLC (high performance liquid chromatography) or combinations thereof. Antibody fragments containing the idiotype of the molecule can likewise be produced by known methods. For example, $F(ab')_2$ fragments can be obtained by pepsin digestion of the complete poly- or monoclonal antibody. Fab' fragments can be obtained by, for example, reducing the disulfide bridges of the relevant $F(ab')_2$ fragment, and Fab fragments can be produced, for example, by treating the antibody molecules with papain and a reducing agent.

Any known method for identifying and selecting antibodies, fragments or derivatives thereof can be used. For example in that these can be detected after appropriate labeling when they have bound to isolated or purified antigen, or by immunoprecipitation of the antigen which has been purified, for example, on polyacrylamide gels, or by antibodies against the blood group antigens competing with other blood group-specific antibodies for binding to sugar side chains.

However, the present invention also relates to the use of hybridoma cell lines for producing the antibodies or a preparation for the use according to the invention and to a method for producing a preparation for the use according to the invention.

Compositions with such antibodies are used according to the invention for oncoses in animals and humans comprising prevention or prophylaxis, control, diagnosis or treatment thereof.

The use according to the invention of the antibodies is based on the surprising observation that proteins with N-glycosidically bonded saccharides belonging to the blood group-specific antigens of type B2, 3, 4 or type A2 allow various types of tumors to be identified and treated. Experiments have shown that it is not possible to employ any desired glycoproteins for producing the antibodies. Thus, proteins with O-glycosidically bonded saccharides have proven unsuitable. The clinical use of the antibodies according to the invention is thus particularly advantageous especially for a large number of disorders, illnesses and conditions.

Depending on the nature and cause of the illness or disorder to be treated or the condition to be influenced in an animal or human body, it may be desirable to administer the antibody preparation systemically, locally or topically onto or into the relevant tissue or organ. A systemic mode of action is desirable, for example, when different organs or organ systems require treatment. By contrast, a local effect would be considered if only the local manifestations of a tumor are to be influenced.

The relevant antibodies can be administered by every enteral or parenteral administration route known to the skilled worker. Suitable for systemic administration is, for example, the intravenous, intravascular, intramuscular, intraarterial, intraperitoneal, oral or intrathecal route. Possible examples of more local administration are subcutaneous, intracutaneous, intracardiac, intralobar, intramedullary, intrapulmonary or into or onto the tissue to be treated (connective, muscle, nerve, epithelial or bone tissue). Depending on the duration and strength of the immunosuppressant effect to be achieved, the antibody preparations can be administered one or more times, also intermittently, a day for several days, weeks or months and in various doses. An antibody preparation suitable for said administrations can be produced by using the injectable physiologically tolerated solutions in sterile form which are known to the skilled worker. The well known aqueous isotonic solutions, for example saline or an appropriate plasma protein solution without gamma-globulin, are available for producing a solution ready for use for parenteral injection or infusion. The preparation can, however, also be in the form of a lyophilizate or dry product which can be reconstituted with one of the well-known injectable solutions immediately before use under sterile conditions, for example as kit of parts. Final production of an antibody preparation to be used according to the invention for injection, infusion or perfusion takes place by mixing antibodies purified by known methods and complying with the definitions given above with one of said physiologically tolerated solutions which may, where appropriate, be supplemented with known vehicles or ancillary substances (for example serum albumins, dextrose, sodium bisulfite, EDTA).

The amount of antibodies to be administered depends on the nature and severity of the illness or disorder to be treated or of the condition to be influenced and on the type and weight of the relevant patient (animal or human). However, the basis is use of a dosage of 0.5–2, preferably 0.7–1.5, mg/kg of body weight of the relevant antibody per dose unit.

DESCRIPTION OF PREFERRED EMBODIMENTS

The invention is described in detail below with reference to the following experimental report:
Materials and Methods Cell lines: the NM-081 (Goshetal, 1983, InVitro 19, 919–928), MT-450 (Kim 1986, J. Surg. Oncol. 33, 151–165) and MTLN2, MTNL3, MTLy, MTPa, MTC (Nevietal, 1982, J. Natl. Cancer Inst. 68, 507–517; Lichtner et al., 1987, Invasion Metastasis, 7, 73–82) cell lines were grown in DMEM supplemented with 10% FCS (fetal calf serum). The RBA and MTAB lines were purchased from the American Type Culture Collection (ATCC, number CRL 1747 and CRL 1666).

Subtractive immunization: tissue culture cells were harvested with PBS/5 mM EDTA and then washed three times in PBS. For each subtraction, 10 female BalbC/B16 F1 hybrid mice, from which preserum had previously been taken, were injected intracutaneously with $2 \times 10^6$ tumor or tissue culture cells carrying no desired antigens (as tolerogen, against which there is production of antibodies of no interest). After 24 h and after 48 h, each mouse received 200 mg/kg cyclophosphamide by intraperitoneal injection. Three weeks later, the mice received corresponding injections of tolerogen and cyclophosphamide once again. Ten days after this, test bleedings were taken. Three weeks after the last injection of tolerogen, $2 \times 106$ tumor or tissue culture cells for which it is intended to produce antibodies were injected intracutaneously (as immunogen). The immunogen was injected twice more after 3 weeks in each case. Ten days after the last immunization, test bleedings were taken. The test bleedings taken after the tolerogen and immunogen immunizations were compared together with the respective presera, employing cell ELISAs with tolerogen and immunogen as targets. This made it possible to identify the mice in which the immune response to tolerogen was maximally impaired and those in which the immune response to immunogen was maximally enhanced. These mice were selected for production of hybridoma cells. Four weeks after the last test bleeding, the mice were splenectomized and the spleen cells were fused with SP2/0 myeloma cells.

Monoclonal antibodies: hybridoma cells were produced by the method of Harlow and Lane, 1988, Antibodies: A Laboratory Manual; Cold Spring Harbor Laboratory Press. The hybridomas were tested in cell ELISAs for the production of antibodies, using the immunogen as target. Antibodies were produced from conditioned medium of hybridoma cells positive in the ELISA test, using protein G-agarose (Dianova) as affinity column.

Cell ELISA: target cells were harvested using PBS/5 mM EDTA and resuspended in DMEM (Dulbecco's modified Eagle's medium)/10% FCS ($2 \times 10^6$/ml). 50 $\mu$l of antibody test solution were pipetted into each U-shaped well of support plates (96 wells per plate), and 50 $\mu$l aliquots of cells were then added. The mixture of cells and antibodies was incubated at 37° C. for 3 h and then washed three times with 200 $\mu$l aliquots of PBS. Initially bound antibodies were incubated with rabbit anti-mouse antibodies coupled to horseradish peroxidase, and then detected with ABTS (2,2'-azino-di (3-ethylbenzothiazoline-6-sulfonate)).

Immunoprecipitation: cells were labeled by incubation with ($^{35}$S)L-methionine (500 mCi/ml) in methionine-free RPMI medium supplemented with dialyzed FCS for 4 h. For a pulse-chase analysis, cells were incubated with ($^{35}$S)L-methionine (500 mCi/ml) in methionine-free RPMI medium supplemented with dialyzed FCS for 15 minutes, then washed and incubated further with methionine-containing medium. For immunoprecipitations, cells were lyzed in RIPA (radioimmunoprecipitation) buffer, and aliquots were immunoprecipitated with 5 µg of antibodies. To purify proteins which bind to Ulex europaeus lectin, the cells were lyzed with PBS/1% NP40/1 mM PMSF and centrifuged, and the lysates were incubated with Ulex europaeus lectin beads at 4° C. for one hour. The beads were then washed three times with PBS, and the excess buffer was removed. The beads were boiled in 1% SDS/20 mM phosphate at pH 7.0. A 20-fold excess of RIPA buffer was then added, and the supernatant was used for the immunoprecipitation after removal of the Ulex europaeus lectin beads. In experiments in which immunoprecipitated proteins were treated with 0.5 U of N-glycosidase F, 2.5 mU of O-glycosidase or 5 mU of neuraminidase, the antigen-antibody matrix bead complex was initially washed in 100 mM phosphate buffer, pH 7.0. Buffer was removed and then the matrix beads were boiled in 5 µl of 1% SDS/20 mM phosphate, pH 7.0, for 5 minutes. The enzymes were then added in 45 µl of 20 mM phosphate buffer (pH 7.0)/1 mM CaSO$_4$. The efficiency of the enzyme reaction was confirmed by comparison with similar digestive processes on immunoprecipitated CD44v4-v7 protein, which is digested by each of said enzymes. Immunoprecipitated proteins were removed by SDS (sodium dodecyl sulfate) PAGE (polyacrylamide gel electrophoresis). Gels were treated with PPO (2,5-diphenyloxazole) and exposed to X-ray sensitive film material.

Metastasis tests: female w/Fu rats received subcutaneous injections of 5×10$^5$ MT-450 cells in PBS. The animals were monitored regularly until the size of their tumors had reached statutory limits or the rats were moribund. The animals were then sacrificed and autopsies were performed. In therapy experiments with antibodies, rats received injections of tumor cells together with antibodies (200 µg/rat). Thereafter the animals received 200 µg of antibodies subcutaneously at the tumor cell injection site twice a week for four weeks.

[lacuna] grown on support plates with 8 depressed chambers (Nunc). Cells from cell suspensions were fixed on silane-coated support plates using a cytospin centrifuge. In both cases, the cells fixed on the support plates were washed three times with PBS, fixed in 4% paraformaldehyde and then incubated in PBS/10% FCS (FPBS) for 30 minutes. Then an antibody solution (in FPBS) was added, and incubation was continued for 2 h. The cells were then washed three times with PBS and incubated with Texas Red-conjugated rabbit anti-mouse Ig, diluted in FPBS, for 1 h. After two PBS washing steps, the stained cells were mounted on the chamber slides.

Binding to Synthetic Oligosaccharides

Blood group-specific oligosaccharides anchored to a solid matrix (SYNSORB®) were purchased from Chembiomed Ltd. (Edmonton, Canada). The chemical structure of the oligosaccharides is shown in Table 4.

The mAb M-N#1 (0.2 µg in 200 µl PBS/1& BSA) was incubated with 10 mg of loaded (or unloaded as control) SYNSORB® beads at room temperature for one hour. After incubation, the supernatants were collected and tested for reactivity with salivary mucines of blood group B as follows. Immediately after collection, saliva from individuals of blood group B or blood group O was heated in a boiling water bath for 15 minutes and then centrifuged as 13,000 g for 5 minutes. The clear supernatant was diluted with 1:80 with 0.1 M carbonate buffer pH 9. ELISA plates (NUNC immunoplates) were incubated with this dilution at room temperature for 1 hour. After the plates had been washed with PBS they were incubated with PBS, 3 BSA. 100 µl portions of the supernatants after absorption of M-N#1 to the SYNSORB® beads were pipetted in duplicates onto the coated ELISA plates. After incubation at 0° C. overnight, the plates were washed with PBS and then incubated with 100 µl of goat anti-mouse IgG bound to alkaline phosphatase (Sigma, St. Louis, Mo., USA) at room temperature for 1 hour. After washing with PBS, bound antibodies were detected using p-nitrophenyl phosphate (Sigma).

Results and Discussion

It was possible by subtractive immunization to produce monoclonal antibodies which react specifically with epitopes on metastasizing tumors of rat mammary carcinoma cell lines. Mice were initially immunized with the non-metastasizing rat mammary carcinoma cell line NM-081 (as tolerogen). After one or two days, the mice were treated with cyclophosphamide in order to kill the activated immune cells. After three weeks, the injection of tolerogen and cyclophosphamide was repeated. After a further three weeks, the metastasizing rat mammary carcinoma cell line MT-450 was administered (as immunogen) to the mice. The efficiency of the immunization and of the cyclophosphamide treatment was tested by cell ELISAs with sera taken in each case before or after treatment with tolerogen, cyclophosphamide or immunogen, using NM-081 cells or MT-450 cells as targets. No serum showed an immune reaction to the tolerogen 10 days after the second immunization and cyclophosphamide treatment, demonstrating the efficiency of the cyclophosphamide treatment. However, all these sera showed an enhanced reactivity toward the immunogen.

Spleen cells from immunized mice were used to generate hybridomas. None of the hybridomas produced antibodies which recognized the tolerogen alone with the effectiveness of the subtractive immunization.

Figure 1:
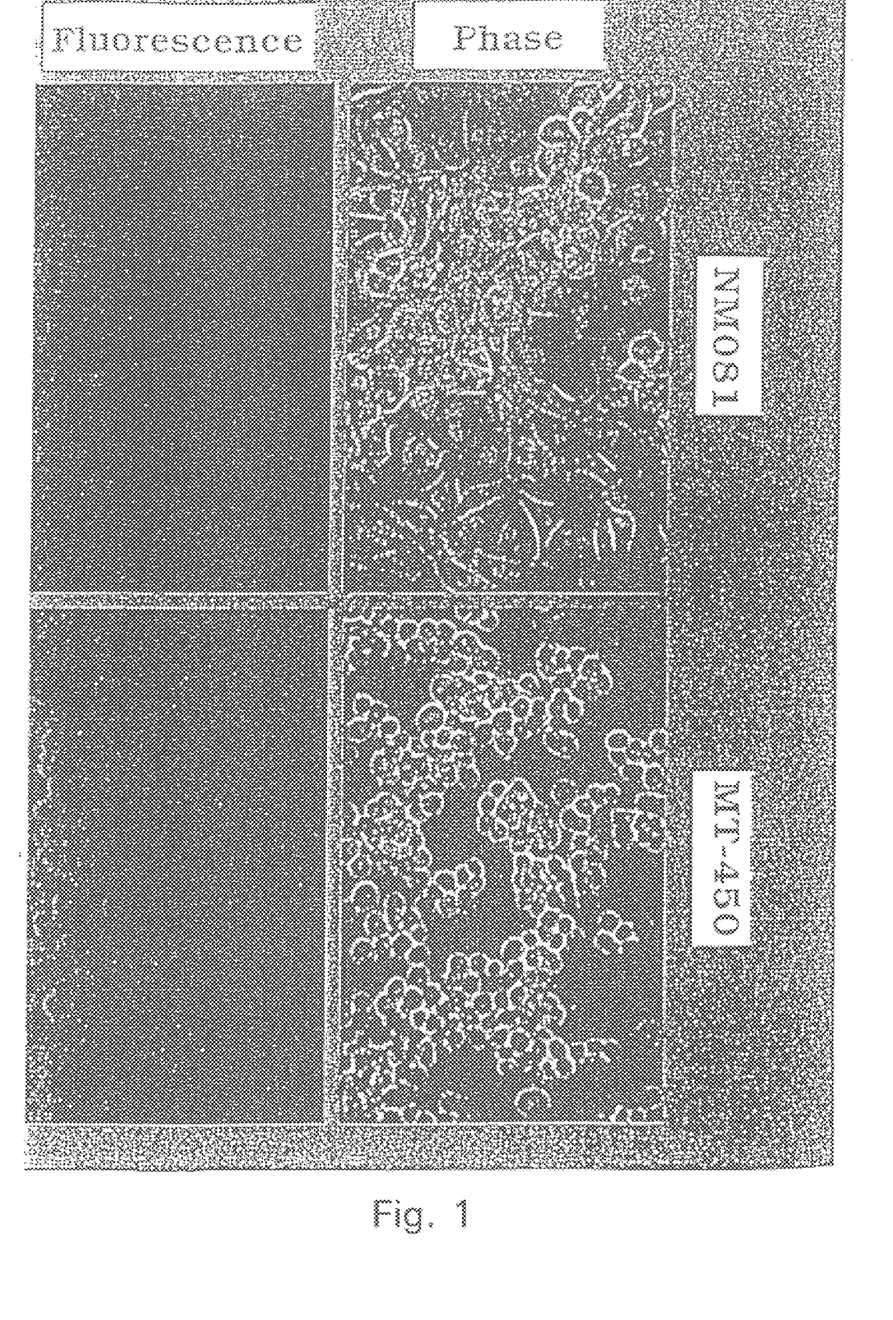

One of the hybridomas produced an antibody (M-N#1) which reacted specifically only with the metastasizing MT-450 cell line in cell ELISAs. This antibody also shows immunofluorescence staining with MT-450 cells (FIG. 1) and can be used for immunoprecipitation. However, it shows no reactivity in Western blots.

Figure 2:
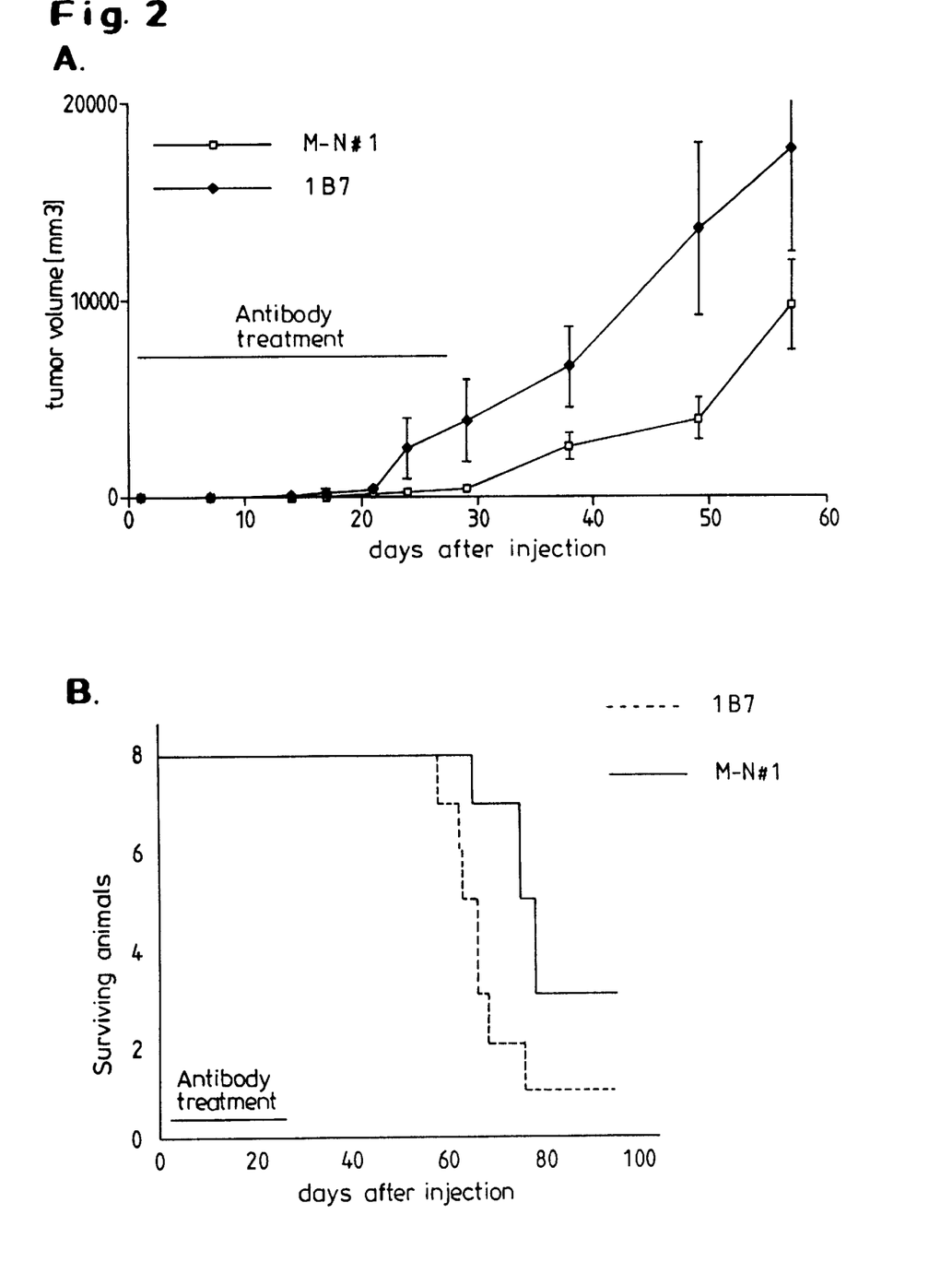

In order to check whether the antibody not only recognizes a metastasis-specifically expressed epitope but is also able to suppress tumor metastasis, MT-450 cells were injected into rat mammary tissue and then treated either with the M-N#1 antibody or with a control antibody of the same isotype. The M-N#1 antibody suppressed the growth of the tumors, which led, on the one hand, to development of tumors in fewer animals than in the control and, on the other hand, to the tumors which grew being distinctly smaller than in the control animals. In addition, the antibody had an inhibitory effect on metastasis growth in the lymph nodes of the tumor-bearing animals. Moreover, the survival period of the animals treated with the M-N#1 antibody was distinctly longer than for control animals (FIG. 2).

Figure 3:
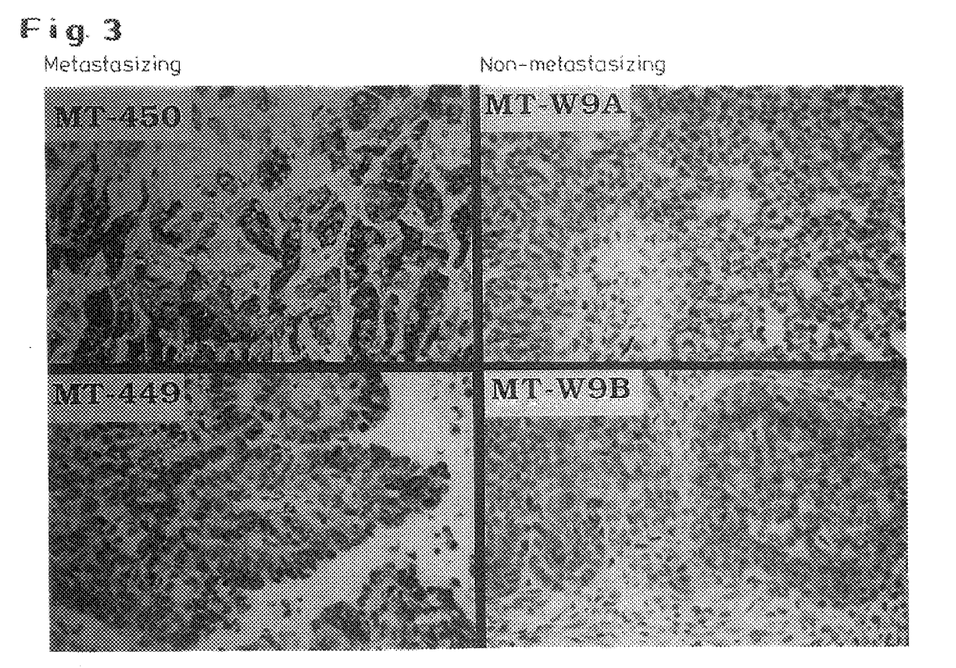

To check the specificity of the M-N#1 antibody, immunohistological staining with M-N#1 antibodies was carried out with various mammary tumor cell lines in tissue culture and tumors of the MT-W9 mammary tumor series, in which there are lines which differ in metastasis potential, in tissue sections (FIG. 3). Of the tumors of the MT-W9 series, the antibodies reacted with the metastasizing MT-450 and MT-449, but not with the non-metastasizing MT-W9A and MT-W9B. Of the cells in culture, none of the lines with low metastasis potential reacted (Table 1). Of the metastasizing mammary carcinoma cell lines, some reacted with the antibody, but some did not. These means that expression of the M-N#1 epitope is not obligatory for the metastasis process for all tumors.

Figure 4:
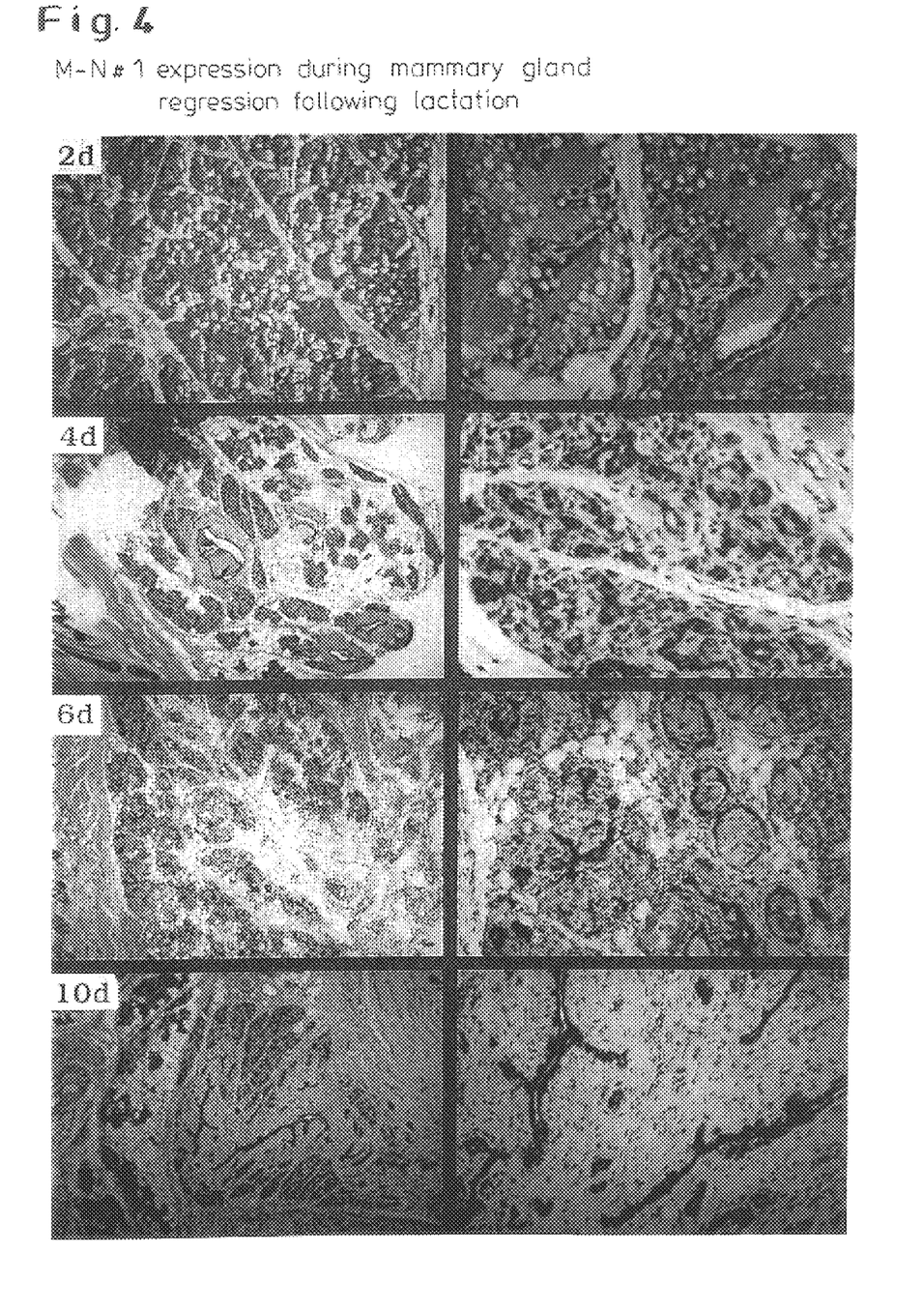

In order to establish whether the M-N#1 antigen is also expressed under physiological conditions in animals, a number of rat tissues were investigated for reactivity with the M-N#1 antibody. Epithelial cells with glandular properties reacted positively (Table 2). Leukocytes from the spleen, the thymus or from lymph nodes and macrophages from the peritoneum were negative. In paraffin sections, the epithelium of the corpus and antrum regions of the stomach, the acinar cells of the pancreas and the basal cells of the intestinal crypts were stained. Strong reactivity was also found in bone marrow. One reason for expression of the M-N#1 epitope on metastasizing mammary tumors might be that this antigen occurs on mammary tissue even under normal physiological conditions. Normal mammary tissue shows no reaction with the M-N#1 antibody, not even during pregnancy and lactation. Interestingly, strong expression of the M-N#1 epitope is found two days after the end of lactation, at the start of mammary regression and during the regression phase (FIG. 4).

Figure 5:
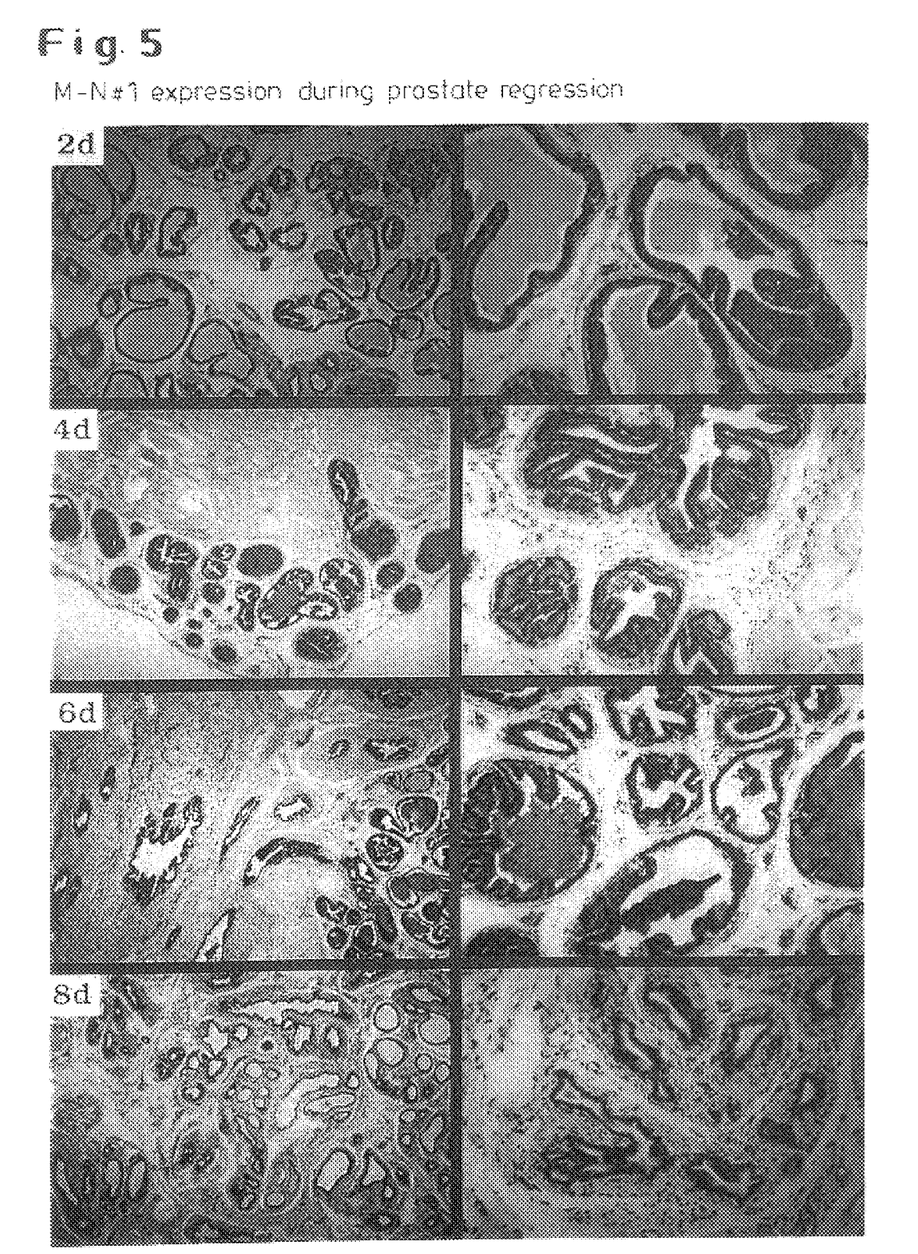

One characteristic of this regression phase is the removal of cells by apoptosis (programmed cell death). Regression of other organs is also possible by apoptosis. These include the prostate gland after castration. The tissue of the prostate gland shows, like normal mammary tissue, no expression of the M-N#1 epitope. Strong expression of M-N#1 antigen is found only two days after castration, with the start of regression of the gland, and this expression is maintained during the regression period (FIG. 5). These data suggest that the M-N#1 antigen is expressed on apoptotic tissue.

Figure 6:
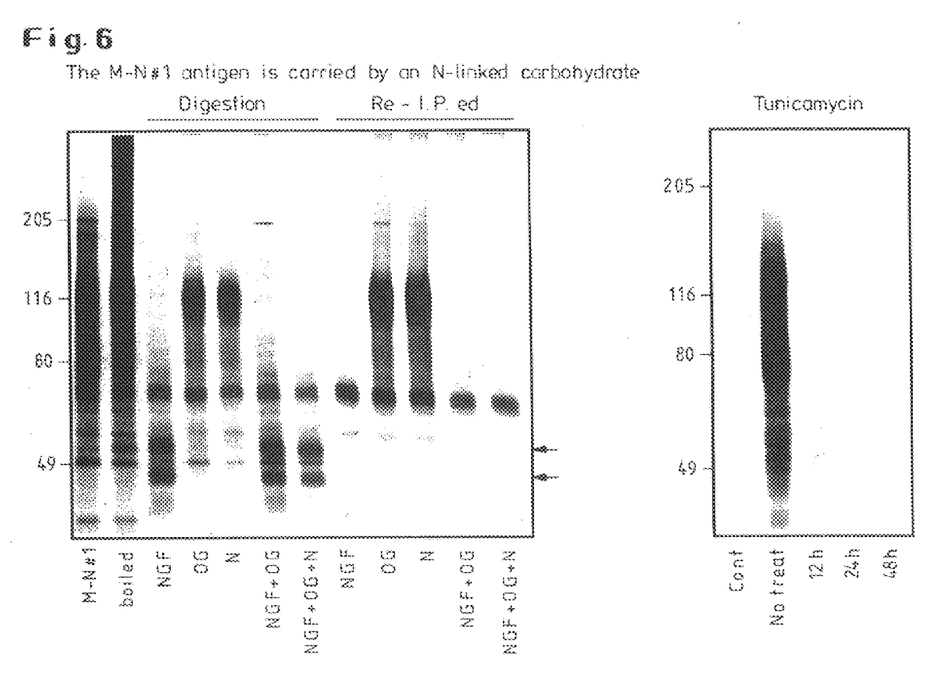

To identify the antigen with which the M-N#1 antibody interacts, reactive material was immunoprecipitated from a cell lysate using M-N#1 antibody, and then the precipitated material was fractionated by gel electrophoresis. The precipitated material was not fractionated into separate bands, but was visible as a "smear", suggesting that the material might have undergone post-translational modification. The immunoprecipitated material was therefore subjected to treatment with various glycosidases. Only treatment with N-glycosidase F had an effect and led to a reduction of the "smear" to two bands with an apparent molecular weight of 49/51 kD (FIG. 6). Chondroitin sulfate and heparan sulfate modifications were ruled out.

Interestingly, M-N#1 antigen could no longer be immunoprecipitated with M-N#1 antibodies after treatment with N-glycosidase F. Since the immunoprecipitability of the M-N#1 antigen was not impaired after thermal treatment of the MT-450 lysate, the antigen recognized by M-N#1 is probably a sugar residue. This was confirmed by treatment of the MT-450 cells with tunicamycin also leading to loss of the immunoprecipable material (FIG. 6).

Figure 7:
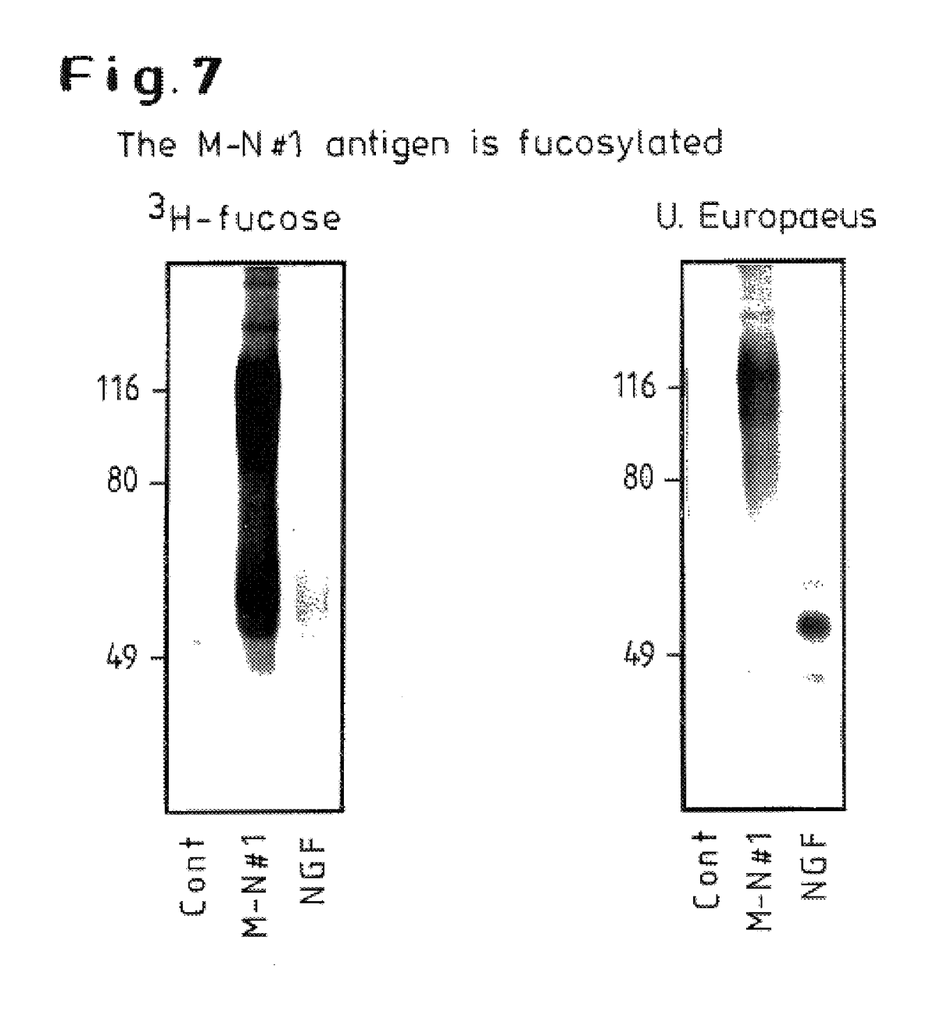
Figure 8:
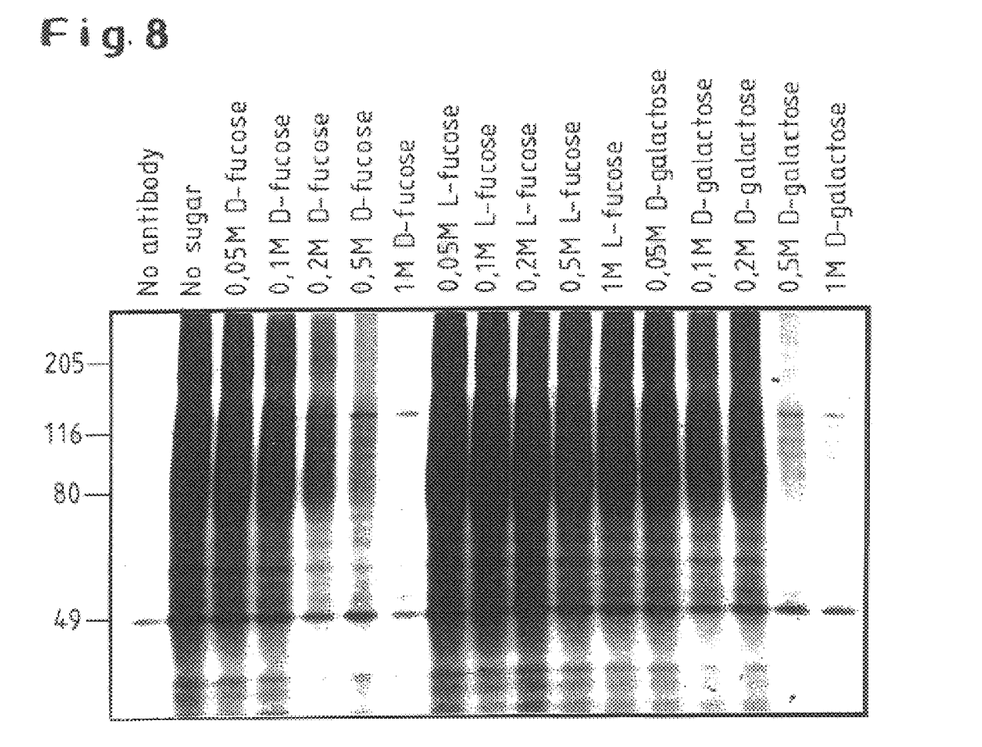

It was shown by labeling MT-450 cells with radioactive fucose that the N-glycosidically bonded sugar recognized by the M-N#1 antibody is fucosylated: i) proteins with a similar molecular weight to those from $^{35}S$-labelled cells were precipitated by the antibody from lysates of fucose-labelled cells (FIG. 7). ii) Treatment of the immunoprecipitated proteins with N-glycosidase F leads to elimination of the fucose (FIG. 7). iii) Purification of fucosylated proteins with Ulex europaeus lectin and subsequent immunoprecipitation with M-N#1 antibody identified proteins with similar molecular weight as after $^{35}S$ labelling (FIG. 7). iv) Protein binding to M-N#1 antibody is inhibited by increasing amounts of D-fucose and D-galactose. L-Fucose has no effect on the binding (FIG. 8). v) The reactivity of the M-N#1 antibody with human erythrocytes and vascular endothelium depends on the blood group status. Reactivity is found with erythrocytes from B and AB individuals (not shown) and with epithelium from the pylorus and duodenum of B individuals if they secrete blood group antigen. For A individuals, reaction is found with epithelium from the pylorus but not from the duodenum and jejunum or erythroyctes if the individuals secrete blood group antigen (Table 3). vi) Finally, the M-N#1 antibody binds in ELISA experiments to human saliva from blood group B individuals. This binding can be blocked by synthetically prepared blood group saccharide of type B2, 3, 4 and of type A2, but not by type B1, A1, 3, 4 or H. The blocking of the binding is dependent on 1–2 bound fucose (Table 5).

TABLE 1

Immunofluorescence staining of rat mammary carcinoma cells

| Cell lines | Metastasis potential | 5G8 | 1.1ASML | M-N#1 |
|---|---|---|---|---|
| MTLN2 | ++ | +++ | +++ | − |
| MTLN3 | +++ | ++ | ++ | − |
| MTC | + | +++ | +(+) | − |
| MTLy | +++ | ++ | ++ | ++* |
| MTPA | + | ++ | (+) | − |
| RBA | +++ | ++ | +(+) | − |
| MAT B | +++ | +++ | +++ | ++* |

Immunofluorescence Staining

The cell lines were stained using the CD44-specific antibodies 5G8 and 1.1. ASML (Sleeman et al., Cancer Research 56, 3134–3141, 1996) and the M-N#1 antibody. The staining intensity was determined subjectively on a four-point scale (−, no staining, +++, strong staining). The metastasis potential corresponds to the classification undertaken in the publication by Sleeman et al., 1996, Cancer Res. 56, 3134–3141. About 10% of the cells were strongly stained.

TABLE 2

Immunohistological staining of normal tissues

| Tissue | M-N#1 staining |
|---|---|
| MT.450 tumor | +++ |
| Brain | − |
| Kidney | − |
| Muscle | − |
| Skin | − |
| Heart | − |
| Lung | − |
| Liver | − |
| Lymph node | − |
| Thymus | − |
| Spleen | − |
| Testis | − |
| Ovary | − |
| Cervix | (+) |
| E12,5 embryo | − |
| Pancreas | +++ |
| Gastrointestinal tract: tongue | − |
| Gastrointestinal tract: esophagus | − |
| Gastrointestinal tract: stomach - cardia | − |
| Gastrointestinal tract: stomach - main stomach | +++ |
| Gastrointestinal tract: stomach pylorus | +++ |

TABLE 2-continued

Immunohistological staining of normal tissues

| Tissue | M-N#1 staining |
|---|---|
| Gastrointestinal tract: duodenum | (+) |
| Gastrointestinal tract: ileum | + |
| Gastrointestinal tract: cecum | − |
| Gastrointestinal tract: colon | + |
| Breast adipose tissue | − |
| Salivary gland | + |
| Bone marrow (femur) | +++ |

Paraffin sections were stained immunohistochemically using M-N#1 antibodies (material and methods) and assessed subjectively on a four-point scale (see Table 1).

TABLE 3

Immunoperoxidase staining with M-N#1 antibodies of the gastroduodenum of individuals phenotyped for the blood group status ABO secreting or nonsecreting

| Phenotype of the donors | Pylorus Surface epithelium | Pylorus Gland | Duodenum Surface epithelium | Duodenum Brünner's gland |
|---|---|---|---|---|
| A nonsecreting | − | − | − | − |
| B nonsecreting | +++[a] | −/+++[b] | − | ++/− |
| O nonsecreting | − | − | − | − |
| A secreting | +++/−[c] | − | − | − |
| B secreting | ++++ ++++/− | +++/− | ++++ | |
| O secreting | − | − | − | − |

[lacuna]
[c]Strong staining of the overwhelming majority of cells.

TABLE 4

Structure of ABH-related oligosaccharides used in the binding studies

| Name | Chemical structure |
|---|---|
| B Disaccharide | Galα1-3Galβ1-R |
| B Trisaccharide | Galα1-3(Fucα1-2)Galβ1-R |
| B Type 1 | Galα1-3(Fucα1-2)Galβ1-3GlcNAcβ1-R |
| B Type 2 | Galα1-3(Fucα1-2)Galβ1-4GlcNAcβ1-R |
| B Type 3 | Galα1-3(Fucα1-2)Galβ1-3GlcNAcα1-R |
| B Type 4 | Galα1-3(Fucα1-2)Galβ1-3GlcNAcβ1-R |
| B linear Trisaccharide | Galα1-3Galβ1-4GlcNAcβ1-R |
| A Type 1 | GalNAcα1-3(Fucα1-2)Galβ1-3GlcNAcβ1-R |
| A Type 2 | GalNAcα1-3(Fucα1-2)Galβ1-4GlcNAcβ1-R |
| A Type 3 | GalNAcα1-3(Fucα1-2)Galβ1-3GalNAcα1-R |
| A Type 4 | GalNAcα1-3(Fucα1-2)Galβ1-3GalNAcβ1-R |
| A Le[b] | GalNAcα1-3(Fucα1-2)Galβ1-3(Fucα1-4)GlcNacβ1-R |
| A Le[y] | GalNAcα1-3(Fucα1-2)Galβ1-4 (Fucα1-3)GlcNacβ1-R |
| H Type 1 | Fucα1-2Galβ1-3GlcNAcβ1-R |
| H Type 2 | Fucα1-2Galβ1-4GlcNAcβ1-R |
| H Type 3 | Fucα1-2Galβ1-3GlcNAcα1-R |
| H Type 4 | Fucα1-2Galβ1-3GlcNAcβ1-R |

R = (CH$_2$)$_8$—CO—NH-Chromosorb

TABLE 5

Binding of M-N#1 to solid-coupled oligosaccharides

| Antigen | % Adsorption |
|---|---|
| B tri | 93 |
| B Type 1 | 0 |
| B Type 2 | 97 |
| B Type 3 | 97 |
| B Type 4 | 98 |
| B Type 5 | 68 |
| Control | 0 |

The binding of M-N#1 antibodies to oligosaccharides fixed on a solid matrix is described in material and methods.

DESCRIPTION OF THE DRAWINGS

FIG. 1

Immunofluorescence staining of NM-081 and MT-450 cells using the M-N#1 antibody. Only the MT-450 cells are stained by the antibody (red immunofluorescence).

FIGS. 2A and 2B.

Effect of the M-N#1 antibody on tumor growth and survival of tumor-bearing rats.

Depiction of tumor growth in FIG. A. (volume of the primary tumor) and survival in FIG. B. of Wistar Furth rats which received subcutaneous injections of 5×105 MT-450 cells and were then treated twice a week with 200 μg of control antibody (IB7) or M-N#1 each time.

FIG. 3

Immunohistochemical staining of paraffin sections of tumors of the MT series using M-N#1 antibodies.

FIG. 4

Immunohistochemical staining of paraffin sections of mammary tissues from female BDX rats after the end of lactation using M-N#1 antibodies. The young rats were removed at time 0. Tissue removal at days 2, 4, 6, and 10.

FIG. 5

Immunohistochemical staining of paraffin sections of rat prostate tissue using the M-N#1 antibody. Male BDX rats were castrated on day 0, and prostate tissue was removed at the stated times (days 2, 4, 6, 8) and stained with M-N#1 antibodies.

FIG. 6

The M-N#1 antigen is part of an N-glycosidically bonded sugar residue. Radiolabelled cell lysates from MT-450 cells were immunoprecipitated with M-N#1, and the precipitated proteins were fractionated on an SDS acrylamide gel.

M-N#1 precipitated proteins migrate as a smear (1st lane). The letters indicate the treatment of the immunoprecipitates before the gel electrophoretic separation: NGF: N-glycosidase F; OG: O-glycosidase; N: neuraminidase. Re-IP.ed means that the enzyme-treated immunoprecipitates were "reprecipitated". The right-hand side of the figure shows the result of a tunicamycin treatment. M-N#1-T450 cells were treated with tunicamycin for the stated time before labelling with radioactive methionine and were immunoprecipitated after labelling. The control represents a precipitation without antibody.

FIG. 7

Demonstration of the fucosylation of the M-N#1 antigen. MT-450 cells were labelled with radioactive fucose, and proteins in lysates of these cells were precipitated with M-N#1 (control precipitation without antibody). Fractionation of the precipitated proteins on SDS polyacrylamide gels is depicted. NGF (N-glycosidaseF) indicates immunoprecipitated proteins treated with NGF before the fractionation. For the experiment "U.europaeus" (right-hand side of the figure), MT-450 cells were labelled with $^{14}$C-methionine, and the extracts were purified on a Ulex europaeus lectin column. Bound proteins were eluted and precipitated without antibody (cont) or with M-N#1 antibodies. NGF indicates N-glycosidaseF treatment.

FIG. 8

Competition of M-N#1 binding with fucose and galactose. Proteins in lysates from radiolabelled ($^{14}$C-methionine) MT-450 cells were immunoprecipitated with M-N#1 antibodies in the absence or with increasing concentrations of fucose or galactose and were fractionated by gel electrophoresis.

What is claimed is:

1. A composition for identifying and suppressing the growth of tumor cells comprising monoclonal M-N#1 antibodies which are from the cell culture with the deposit number DSM ACC 2333 and react with proteins which have N-glycosidically bonded saccharides, wherein the saccharides belong to the blood group-specific antigens of type B2, B3, or B4 or type A2.

2. A pharmaceutical composition comprising the antibodies of claim 1 for enteral, parenteral, systemic, local and/or topical administration.

3. A pharmaceutical composition comprising the antibodies of claim 1 for injection, infusion or perfusion.

4. A method for the diagnosis of mammary tumors, comprising the step of administering the composition of claim 1.

5. A method for the treatment of mammary tumors by inhibition of growth and metastasis of said tumors, comprising the step of administering the composition of claim 1.

* * * * *